United States Patent
Tirumalai et al.

(10) Patent No.: US 6,872,181 B2
(45) Date of Patent: Mar. 29, 2005

(54) COMPOUND IMAGE DISPLAY SYSTEM AND METHOD

(75) Inventors: Arun P. Tirumalai, Issaquah, WA (US); Patrick L. Sutcliffe, Sammamish, WA (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 708 days.

(21) Appl. No.: 09/842,384

(22) Filed: Apr. 25, 2001

(65) Prior Publication Data

US 2002/0167533 A1 Nov. 14, 2002

(51) Int. Cl.[7] .................................................. A61B 8/00
(52) U.S. Cl. ...................................................... 600/447
(58) Field of Search ..................... 600/437, 440–441, 600/443, 447, 455, 456, 458; 128/916; 73/626

(56) References Cited

U.S. PATENT DOCUMENTS

| | | |
|---|---|---|
| 5,353,354 A | 10/1994 | Keller et al. |
| 5,566,674 A | 10/1996 | Weng |
| 5,575,286 A | 11/1996 | Weng et al. |
| 5,782,766 A | 7/1998 | Weng et al. |
| 5,910,114 A | 6/1999 | Nock et al. |
| 6,014,473 A | 1/2000 | Hossack et al. |
| 6,299,579 B1 * | 10/2001 | Peterson et al. ............ 600/443 |
| 6,364,835 B1 * | 4/2002 | Hossack et al. ............ 600/443 |

* cited by examiner

*Primary Examiner*—Francis J. Jaworski

(57) ABSTRACT

A method and system for displaying an image associated with an extended field of view is provided. One image comprises a compounded sub-set of the extended field of view. Other images may include an extended field of view image or an image absent compounding from the extended field of view image. The compounded sub-set image is associated with reduced noise as compared to the image absent compounding and more closely resembles an area of the extended field of view image. Where plurality of images are associated with a rotated transducer or scan planes or where a sector or Vector® scan pattern is used, the compounded sub-set provides spatial compounding associated with different angles of incidence to the region of interest, increasing speckle reduction.

21 Claims, 3 Drawing Sheets

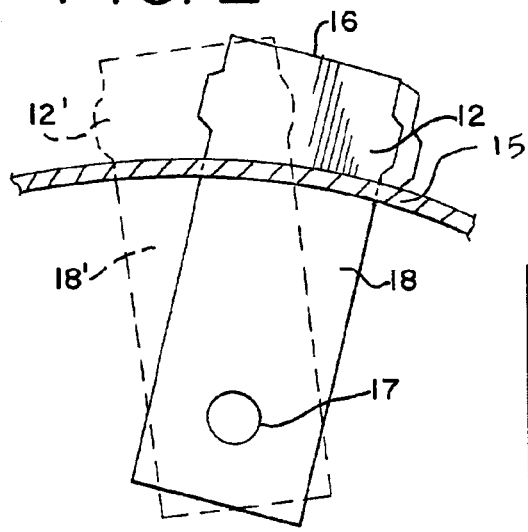
FIG. 2
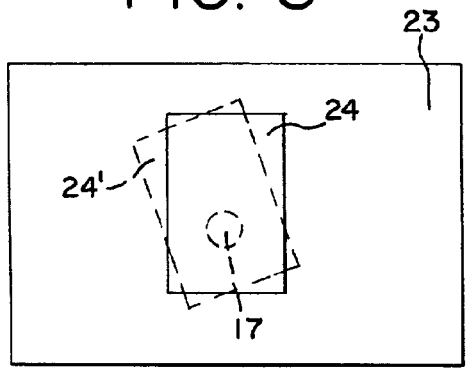
FIG. 3
FIG. 4
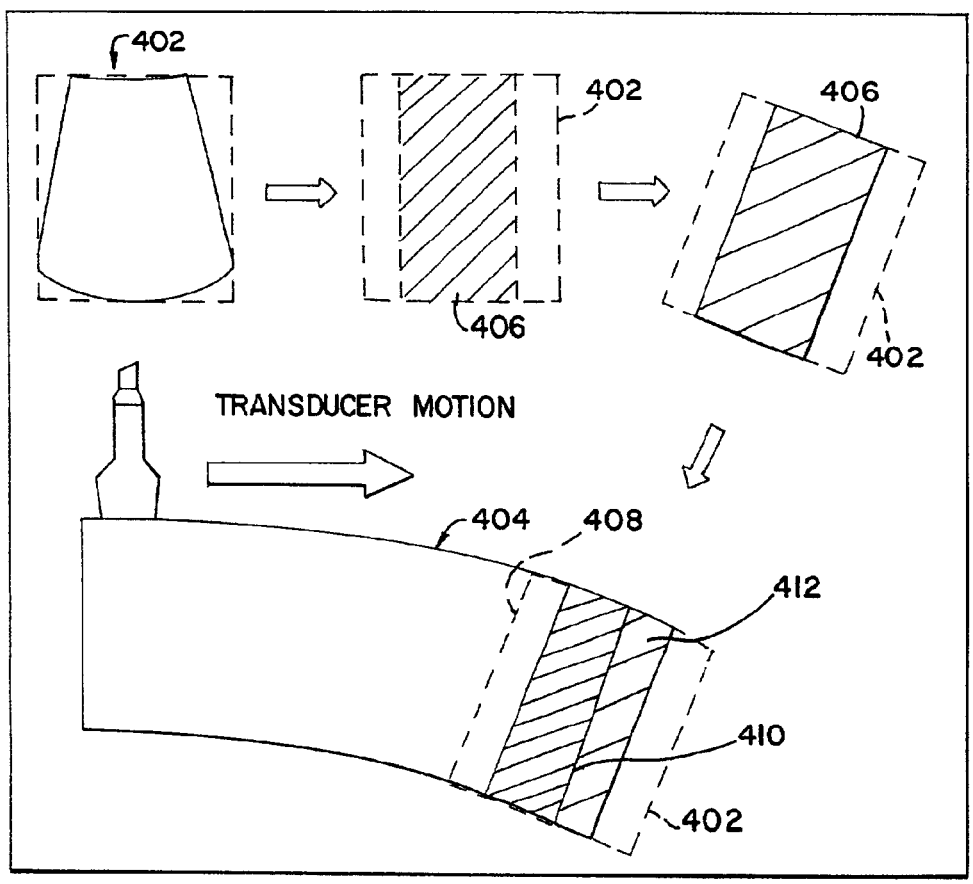

COMPOUND IMAGE DISPLAY SYSTEM AND METHOD

BACKGROUND

This invention relates to spatial compound imaging. In particular, displays associated with images compounded from scans of different areas are provided.

Extended field of view (i.e., panoramic) imaging provides compound imaging. U.S. Pat. Nos. 5,566,674, 5,575,286, 5,782,766 and 6,014,473 describe various techniques for extended field of view imaging. In general, a transducer is moved along an azimuthal dimension to acquire frames of data associated with different transducer positions within an imaging plane. One of various techniques are used to determine the position of each frame of data relative to other frames of data. The frames of data are spatially aligned and combined to form the extended field of view image. The combination may include compounding data representing same locations.

Typically, the extended field of view image is shown on a display. Associated images may also be generated. In one configuration shown in U.S. Pat. No. 5,782,766, a region of the extended field of view image may be selected. Stored image data used to form the extended field of view image is then used to generate an image adjacent to the extended field of view image. The stored image data corresponds to the selected region, but without compounding for the extended field of view. The stored image may include undesirable noise and/or look different than the corresponding region of the extended field of view image.

BRIEF SUMMARY

The present invention is defined by the following claims, and nothing in this section should be taken as a limitation on those claims. By way of introduction, the preferred embodiment described below includes a method and system for displaying a compounded image. The compounded image is extracted from data for an extended field of view. The compounded image comprises a compounded sub-set of the extended field of view data. Other images may include an extended field of view image or an image absent compounding for forming the extended field of view data.

The compounded sub-set image is associated with reduced noise as compared to the image absent compounding and more closely resembles an area of the extended field of view image. Where a plurality of images are associated with a rotated transducer and scan planes or where a sector or Vector® scan pattern is used, the compounded sub-set provides spatial compounding associated with different angles of incidence to the region of interest, increasing speckle reduction.

In a first aspect, a method for displaying a plurality of images of an extended field of view associated with azimuthal transducer movement is provided. A first frame of data is compounded with a second frame of data in an overlapping region where the first and second frames are associated with first and second different transducer positions, respectively. An extended field of view image responsive to the compounding is displayed. A compounded image comprising a sub-set of image data from the extended field of view image is also displayed. The compounded image is displayed adjacent to the extended field of view image.

In a second aspect, a method for displaying a plurality of images of an extended field of view associated with azimuthal transducer movement is provided. A first frame of data is compounded with a second frame of data in an overlapping region where the first and second frames are associated with first and second different transducer positions, respectively. A compounded image comprising a sub-set of image data responsive to the compounding is displayed. A first image responsive to the first frame of data absent the compounding is displayed adjacent to the compounded image.

In a third aspect, a transducer, processor and display are provided for performing the methods of the first and/or second aspects.

In a fourth aspect, a method for displaying an image extracted from extended field of view data associated with azimuthal transducer movement is provided. A first frame of data is compounded with a second frame of data in an overlapping region where the first and second frames are associated with first and second different transducer positions, respectively. A compounded image comprising a sub-set of data responsive to the compounding and corresponding to at least a portion of the overlapping region is displayed.

Further aspects and advantages of the invention are discussed below in conjunction with the preferred embodiments.

BRIEF DESCRIPTION OF SEVERAL VIEWS OF THE DRAWINGS

FIG. 2 is a side sectional view of one embodiment of an ultrasound transducer manipulated spatially to obtain incoherent images of a region of interest;

FIG. 3 illustrates an image display of a current image frame in one embodiment;

FIG. 4 illustrates one embodiment of compounding frames of data to form an extended field of view image.

DETAILED DESCRIPTION OF THE PREFERRED EMBODIMENTS

To provide diagnostic information, information for an extended field of view is obtained. The information includes two or more frames of data associated with scans of a patient corresponding to two or more transducer positions, respectively. The frames of data are compounded together to reduce speckle. Various images are provided using this information, such as an extended field of view image corresponding to the compounded frames of data, a compounded image corresponding to a sub-set of the extended field of view compounded information or an image corresponding to one of the frames of data absent the compounded for forming the extended field of view. These images and comparison between these images assists in medical diagnosis.

Figure 1:
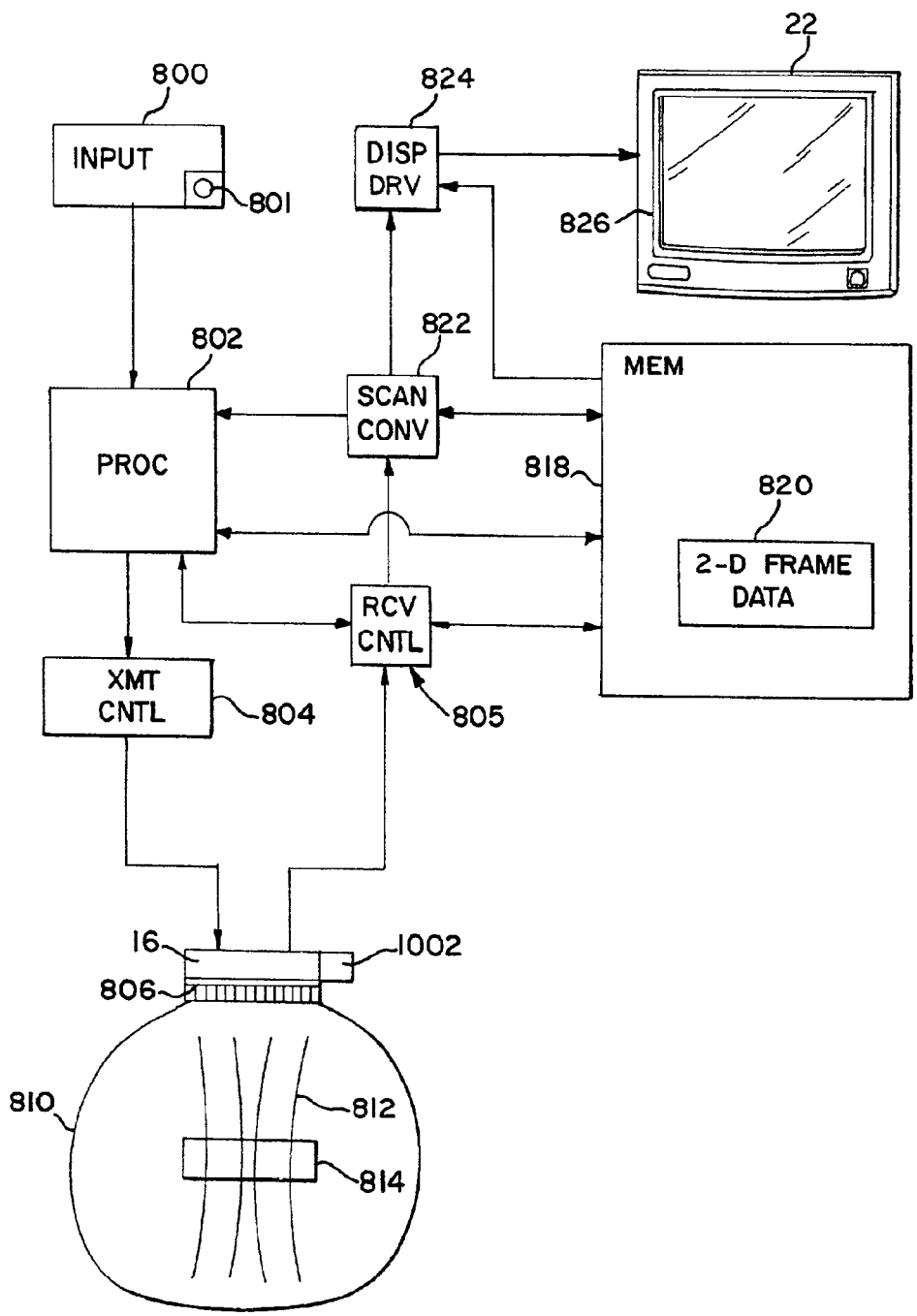
FIG. 1 is a block diagram of one embodiment of an ultrasound system for generating a compounded image.

FIG. 1 illustrates an ultrasonic imaging system according to one embodiment. The system includes an input 800, a processing system 802, a transmission control 804, a transducer 16 with transducer elements 806, a display 22, a receive control 805, a scan converter 822, a memory 818, a display driver 824 and a display 22. The system may comprise a Sonoline®, Sequoia, Aspen, 128XP or another ultrasound system. Other medical diagnostic ultrasound systems may be used, such as from other manufacturers. In alternative embodiments, other imaging systems, such as MRI systems, CAT scan systems, x-ray systems, photographic or systems designed for flaw detection, may be used.

The input unit 800 includes one or more of a keyboard, knobs, buttons, and a cursor-control device, such as a trackball 801 or mouse. The input unit 800 is connected to the processing system 802 for receiving user input and configuration information.

The processing system 802 includes an electrically connected and cooperating group of processors, such as microprocessors and digital signal processors. For example, the processing system 802 includes application specific integrated circuits, look-up-table memories and/or general processors for B-mode processing, Doppler processing, filtering, other data processing functions and/or control processing. In an alternative embodiment, the processing system 802 is implemented by a single high speed processor. The processing system 802 detects information from electrical signals and generates image information. The processing system 802 also sets, adjusts, and monitors the operating parameters of other components of the ultrasound system, such as the transmission control circuit 804.

The transmission control circuit 804 comprises a transmit beamformer. The transmission control circuit 804 generates and applies electrical control and driving signals to the transducer 16. By varying the phasing, amplitude, and timing of the driving signals, ultrasonic waves are focused to form a series of scan lines 812. A scanned region of interest is shown as an interrogation region or volume 814. The format of the scan lines 812 and the resulting interrogation region 814 may be any of a sector scan, a Vector® scan, a linear scan or other scan.

For extended field of view imaging, sector or Vector® scans provide further speckle reduction in response to compounding. Multiple fields of view from different angles relative to a same location in the patient are provided as the transducer 16 is moved along an azimuthal direction. The information associated with different scan angles are compounded, reducing speckle. Alternatively, linear scans associated with rotation of the transducer 16 in the imaging plane provide information for the same location from different angles as shown in FIG. 2.

The transducer 16 comprises an array of elements 806, such as piezoelectric or microelectromechanical (MEM) elements. The elements 806 convert between ultrasonic and electrical energy. By placing the transducer 16 against the body of a patient, the ultrasonic waves enter a portion 810 of the patient's body. Ultrasonic echoes from the waves transmitted into the body return to the transducer 16.

Electrical signals responsive to the echoes are provided to the receive controller 805. The receive controller 805 comprises a receive beamformer for amplifying, down converting to low frequencies and converting analog information to digital information. The receive controller 805 may be integrated into the processing system 802 or the transmit controller 804. The receive controller processing may include time-gating, gain compensation and diffraction compensation in order to identify echo signals that correspond to each scan plane of the interrogation volume 814. Alternatively, beamformed information is passed from the receive controller 805 to the processing system 802 for detection, filtering or other processing.

Detected or pre-detected information for the two-dimensional scanned regions are stored in the memory 818 as 2-D frames of data 820. The memory 818 comprises a CINE memory, memory loop, buffer, random access memory, tape memory or other memory device. Each frame of data corresponds to one image frame or one two-dimensional cross section of the interrogation volume 814. Each frame of data and associated scan corresponds to one transducer position. As the transducer 16 is moved in the azimuthal dimension, other frames of data are obtained. Since an entire scan for a frame of data is not instantaneous, some movement of the transducer occurs during acquisition of any single frame of data. As used herein, a frame of data associated with one position of the transducer includes a range of positions associated with movement during a scan. Other frames of data are associated with other or different transducer positions. Each frame of data is separately stored.

The frame of data is also applied to the scan converter 822. The scan converter 822 comprises an application specific integrated circuit or processor for converting the frame of data into display intensity, brightness or color values formatted for the display device 22.

The display device 22 includes or is connected to a display driver 824 and a screen 826. The display device 22 comprises an LCD or CRT device that is divided into an X-Y (or polar) matrix or pattern of picture elements (i.e., pixels). The displayed image is a pattern of pixels that correspond to the frame of data, frames of data compounded to form an extended field of view image or an image corresponding to a sub-set of compounded frames of data.

Ultrasonic imaging is configured in any of several modes. For example, B-mode, power or energy Doppler mode, velocity Doppler mode or other modes are used. The data in any frame of data is responsive to one or more of these modes. B-mode data is typically displayed as gray scale data, and Doppler data is typically displayed as color data.

The ultrasound system described above generates extended field of view data corresponding to compounding overlapping regions for two or more frames of data. The frames of data are associated with different transducer positions. In one embodiment, the processing system 802 or a dedicated sub-system or processor performs the compounding to generate the extended field of view data.

The generation of the extended field of view data is performed as either real-time imaging or re-generation of recorded image information. In application, a physician may use a conventional ultrasonic imaging system to produce frames of data recorded onto a permanent storage medium, such as tape. Subsequently, the frames of data may be processed for later image generation using the imaging system or a remote computer.

FIGS. 2 and 3 illustrate acquisition of frames of data in an extended field of view. A transducer 16 is pressed against a skin surface 15 of a patient as part of an ultrasonic imaging operation. An acoustically conductive lubricating agent may be applied to the skin surface 15 to improve the acoustic coupling between the transducer 16 and the patient. A region of interest 17 lies below the skin surface 15. The region of interest 17 may be completely, partially or not obscured by other tissue disposed between the region of interest 17 and the skin surface 15. To perform the imaging operation of the region of interest 17, the operator manipulates the transducer 16 to various positions along the patient's skin surface 15. The previous position of the transducer is denoted by 12' and the current position is denoted by 12 in FIG. 2.

Frames of data for two scan planes 18, 18' corresponding to the current and previous positions of the transducer 12, 12' are obtained. As shown, each scan plane 18, 18' is responsive to a linear scan format, but sector or other formats may be used so that the region of interest 17 is scanned from more than one angle.

The frames of data representing two-dimensional scans of the patient are processed by the ultrasound system. Two two-dimensional, cross-sectional images 24, 24' are consecutively displayed on the video display terminal 23 of FIG. 3. The current image is superimposed over and replaces the previous image in the same orientation. The frames of data are continuously acquired and displayed in real time. Alternatively, triggered acquisition is used or off-line or non-real time display is provided. In another alternative embodiment, images are not displayed.

One or more frames of data are stored in the memory 818 for spatial compounding during real-time imaging or off-line imaging. Compounding provides a single compounded frame of data or a single image that reflects the particular orientations of the differing images, such as the previous image 24'. To compound two or more frames of data, the relative positions of or motion between the scan planes for the frames of data is determined and then overlapping regions are compounded.

Motion is determined as a function of the frames of data or position information. For example, a position sensor-1002 is attached to the transducer 16, such as accelerometers or magnetic positioning devices. Depending on the chosen sensor, an external reference source may be included, such as for a Polhemus sensor. The relative positions of the transducer 16 are measured with the position sensor.

For the embodiment determining motion as a function of the frames of data, the relative position with the maximum correlation of two frames of data is determined. A reference frame of data is used to determine the relative position of another frame of data. For example, the previous frame of data from scan plane 18' (also referred to herein as image frame n–1) is combined with any previous image frames into a spatially compounded frame of data (the extended field of view data) and used as a reference frame of data. Alternatively, the previous frame of data is used as the reference frame of data. There are two advantages of using the extended field of view data as a reference. First, the extended field of view data has less speckle than the uncompounded frame of data, n–1. The estimation of image frame motion is compromised less due to speckle variation and is more robust in matching deterministic image features. Second, any global accumulative registration error is eliminated so that the user can move the transducer back and forth with reduced likelihood of mismatching.

Motion between the reference frame and the current frame of data (also referred to herein as image frame n or the n'th image frame) is calculated. In one embodiment, the frame of data is divided into smaller regions for estimation of local motion vectors. Local motion vectors are determined by correlating the smaller regions with the reference frame of data. Global motion associated with the frame of data is determined from the local motion vectors using an algorithm or fuzzy logic. This motion estimation technique is taught in U.S. Pat. Nos. 5,566,674, 5,575,286 and 5,782,766, the disclosures of which are incorporated herein by reference.

In other embodiments, the entire frame of data without division or a portion of the frame of data is used for motion estimation. U.S. Pat. Nos. 6,014,473, 6,364,835 (Ser. No. 09/536,215, filed Mar. 27, 2000) and 6,554,770 (Ser. No. 09/648,214, filed Aug. 25, 2000), the disclosures of which are herein incorporated by reference, teach determining position using an entire frame of data or a selected sub-set of the frame of data. The correlation between the frame of data or selected sub-set is determined as a minimum sum of absolute differences and/or other functions.

The estimated motion is then used to geometrically transform the current frame of data, n, to match the orientation and translation of the previous frame of data or reference frame of data. If the rotation is large, the extended field of view data or reference frame of data is rotated back to a zero degree angle before matching with the current frame of data. Otherwise, accounting for large angular differences between the extended field of view data and the current frame of data within the geometric transformation algorithm may be difficult, and in some cases, may double the geometric transformation computation.

FIG. 4 shows transformation and combination of a current frame of data 402 with extended field of view data 404. The current frame of data 402 or a sub-set of data 406 is selected for combination. In one embodiment, the sub-set of data 406 corresponds to a center section, such as associated with data corresponding to a width of 64 pixels, along substantially the entire range dimension. In alternative embodiments, an edge portion, only a portion of the data along the range dimension or other sub-set of data is selected. As shown, the selected frame of data 402 or sub-set of data 406 is rotated and translated (positioned) relative to the reference frame of data 408 or the extended field of view data 404.

Transforming and compounding the sub-set of data 406 may avoid smearing effects due to errors in motion estimation. In one embodiment, the width or other aspects of the selected section and corresponding sub-set of data 406 are selectable by the user. For example, the user selects from a list of width options or provides incremental input for adjusting the width. Changing the width associated with the sub-set of data 406 changes an amount of compounding. Other compounding aspects may be user selectable, such as the algorithm for combination or the size or format of the region associated with the sub-set of data 406.

Using stored data, the user may have the data recombined responsive to different widths or other aspects for optimal imaging. For recombining each frame of data 402, the position or estimated motion of the frame of data 402 relative to the extended field of view data 404 is stored.

Overlapping regions 410 of the geometrically corrected frames of data or selected portions (sub-sets) of the frames of data are combined. Two examples of techniques that can be applied to combine the corrected frames are: "recursive spatial compounding," which recursively averages the new image frame with existing extended field of view data; and "ramp compounding," which gives weight ramps for both the new image frame and the existing extended field of view data in the overlapping area. This latter technique successfully reduces local discontinuity caused by motion jitters. An example of ramp compounding includes using a linear varying weight that varies as a function of an amount of overlap. Other combination techniques, such as finite impulse response and/or alpha blending techniques, may be used and are described in U.S. Pat. Nos. 6,014,473, 6,364, 835 , (Ser. No. 09/536,215, filed Mar. 27, 2000) and 6,554, 770 (Ser. No. 09/648,214, filed Aug. 25, 2000).

In one embodiment, a recursive averaging algorithm is used to spatially compound the current frame of data or sub-set of data, n, with the existing extended field of view data. The existing extended field of view data may include data responsive to one or a compounded combination of a plurality of frames of data. In the overlapping area 410, the new extended field of view data, EFOV(n), represents the weighted average of the reference frame of data or previous extended field of view data, EFOV(n−1) and the current frame of data or sub-set of data, Input(n), in accordance with the following equation:

$$EFOV(n)=((1-m)(EFOV(n-1))+(m\ Input(n)))$$

where m is a weighting factor and n is the frame number. The weighting factor m ranges from 0 to 1, and is a function of both the frame number n and the frame motion speed estimated from the image registration algorithm described above.

When the spatial compounding process starts, the weighting factor m is mainly controlled by the frame number, n. For small values of the frame number n, the weighting factor m is large. Conversely, after a large number of frames of data, each individual frame of data has less effect on the extended field of view data, so the weighting factor m is smaller. This way, a strong compounding effect in the beginning of the scan allows the extended field of view data to quickly converge to a maximum compounding effect. After a few frames, the weighting factor m becomes smaller, and, eventually, a constant value defined by motion speed is used for the weighting factor.

Different values for the constant weighting factor m can be utilized for high speed, low speed and very low speed. The compounding effect is more reliable where there is high or moderate frame motion speed. If the transducer 16 were kept still for several image frames (i.e., zero frame motion speed) the weight applied to these particular frames should be substantially less so as to not erase the previous extended field of view data. This adaptive averaging technique makes the compounding effect independent from motion speed. The optimal constant value of the weighting factor m can be readily derived from a consideration of various factors, including the intended frame rate, the imaging depth and the transducer rotation. Other algorithms for determining the weight, a constant weight or non-recursive compounding may be used.

For either recursive or non-recursive combination, frames of data for combination may be selected as a function of estimated motion. A new frame of data is compounded with the extended field of view frame of data or another frame of data when a threshold amount of motion, such as translation and/or rotation, is identified. For example, a new frame of data is compounded using a ramp function when the transducer has moved laterally by a minimum amount since the last frame of data used for compounding. In one embodiment, the threshold is set at about a distance associated with 10 pixels, but other distances may be used. If the transducer is moved slowly or held in one position, compounding is limited to avoid erasing or overwriting previous data.

For non-overlapping regions 412, the frame of data 402 or selected sub-set of data 406 is added to the extended field of view data. The extended field of view data is stored in a buffer, the processing system 802 or the memory 818. The non-overlapping region may overlap with subsequent frames of data 402 or sub-sets of data 406. Alternatively, the extended field of view data includes some data not responsive to compounding for forming the extended field of view. In yet other alternative embodiments, the non-overlapping region 412 for the first or last frames of data 402 or sub-sets of data 406 are removed from the extended field of view. In yet other alternative embodiments, any data from the extended field of view data not responsive to compounding is removed.

As discussed above, different images may be displayed. For example, a compounded image comprising a sub-set of the extended field of view data is generated. The compounded image is displayed alone or adjacent one or both of an extended field of view image and an image not responsive to compounding for generating the extended field of view data.

Figure 6:
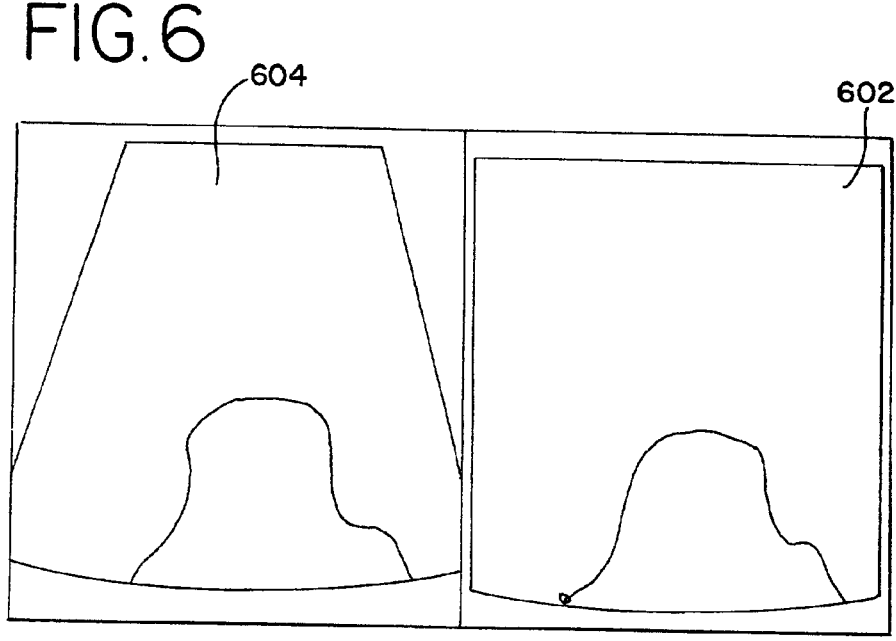
FIG. 6 illustrates one embodiment of adjacent display of one image absent compounded for extended field of view and a compounded image extracted from the extended field of view image.

FIG. 6 shows one embodiment used in real time or off-line for displaying the compounded image 602. Compounded image data extracted from the extended field of view data corresponds to a same region as the most recently acquired frame of data. The compounded image 602 is transformed and displayed adjacent to an image 604 responsive to the most recently acquired frame of data absent compounding for forming the extended field of view data.

Figure 5:
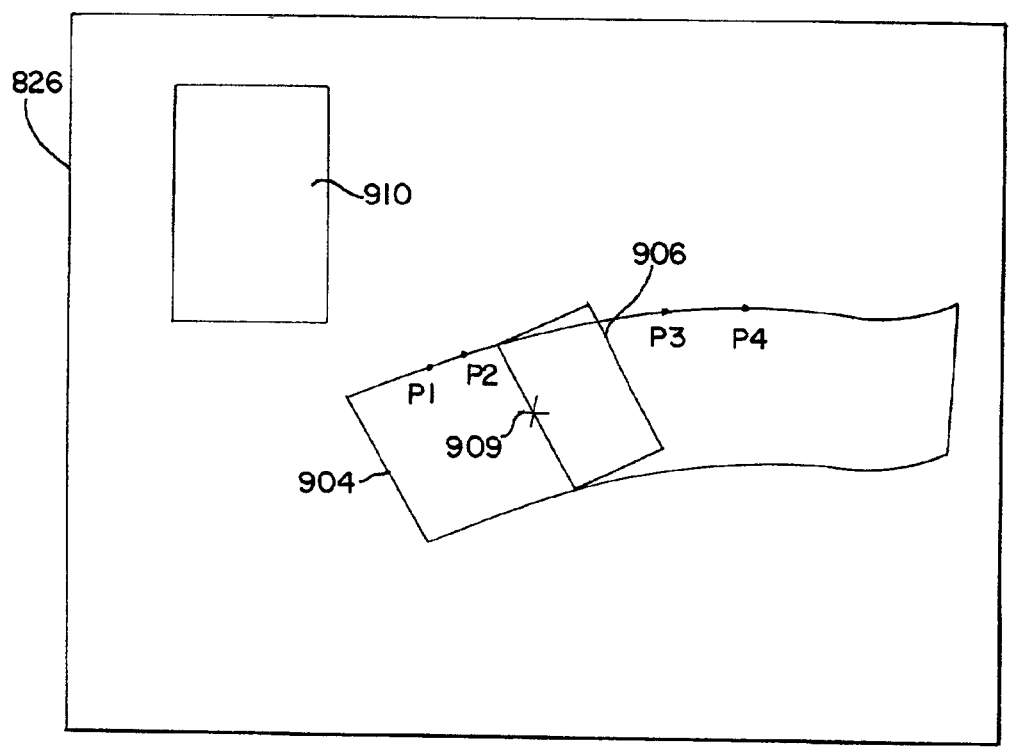
FIG. 5 illustrates one embodiment of a display, including an extended field of view image and an extracted compounded sub-set image.

FIG. 5 shows another embodiment used off-line or in a CINE mode for displaying the compounded image 910. The compounded image data extracted from the extended field of view data corresponds to a selected region 906 on an extended field of view image 904, a selected component image, selected time or a first or last acquired image.

The compounded image 910 is transformed and displayed. In one embodiment, the compounded image 910 is displayed adjacent to the extended field of view image 904 or adjacent to an image corresponding to the selected region but absent the compounding associated with forming the extended field of view data. For example, the compounded image 910, 602 is displayed adjacent to an image 604 generated from a previously acquired frame of data without the compounding associated with the extended field of view image as shown in FIG. 6. In this example, the user may scroll through a plurality of images stored in the memory 818 absent extended field of view compounding as part of a CINE loop. For one or more of the images, data is extracted from the extended field of view data and an associated compound image 602 is also displayed.

The compounded image data is extracted from the extended field of view data as a function of the stored location information. The stored location information provides translation and rotation or the motion estimate used for compounding. The stored location information designates the data for extraction from the extended field of view data. The extracted data corresponds to a region associated with the sub-set 406 of a frame of data 402, the frame of data 402, an area larger than the frame of data 402, an area including part of a frame of data 402 or another area. In one embodiment, a sub-set 406 of a frame of data 402 is compounded with the extended field of view data. For displaying the compounded image, data for an area corresponding to the position and size of the frame of data 402 relative to the extended field of view is extracted.

In one embodiment shown in FIG. 5, the user selects the data for extraction from a displayed extended field of view image 904. The processing system 802, via the display driver 824, generates a cursor 909 on the display responsive to the trackball, mouse or other pointer 801. The cursor position relates to the position of individual pixels in the extended field of view image 904. The position of any given pixel corresponds to a leading or trailing edge of one stored frame of data, such as frame of data 906 corresponding to a particular transducer position. Alternatively, the position of the cursor is related to a center or other location relative to the frames of data. In yet another alternative embodiment, the cursor position is related to an edge of a box not associated with a stored frame, such as being associated with an area corresponding to a similar size as a stored frame of data or a user selected area.

The user may maneuver the pointer 801 to select a frame of data or area of particular interest. The processing system then extracts the sub-set of data corresponding to the area of interest from the extended field of view data for generating the compounded image 910. Additionally, the frame of data associated with the selected location may be recalled from the frame data memory 820 and displayed in an uncompounded form in addition to or in replacement of the extended field of view image.

As an alternative to the cursor-directed frame-selection procedure described above, the user may instead maneuver the input device 801 to recall frames of data from CINE memory. In one embodiment, the processing system 802 causes the display of an outline of each respective frame as a superimposed outline 906 on the extended field of view image 904. Alternatively, an outline and/or the extended field of view image 904 is not displayed. The extended field of view data corresponding to the outline 906 is extracted.

The extracted data for the compounded image 602 is in a same or different format and/or orientation as the data provided for compounding. For example, data for a rectangular or linear area is extracted where the data provided for compounding comprised a sector frame of data, a linear frame of data or a sub-set of data in any format or geometry. As another example, the extracted frame of data is oriented at an angle to a transducer down orientation used to image a frame of data absent compounding for the extended field of view.

The extracted data for the compounded image 602 is transformed. In one embodiment, the extracted data is transformed so that the compounded image 602 is displayed (a) in a same orientation as an adjacent image as shown in FIG. 6 or (b) in a transducer down orientation used in conventional ultrasound system as shown in FIG. 5, (c) in an orientation that is a function of the transducer rotation associated with the estimated motion or (d) in an user selected orientation. In one embodiment, a linear affine warp function is used to transform the extracted data, but other functions may be used. In alternative embodiments, no transformation is used.

As FIG. 5 illustrates, the extended field of view image 904 may represent a view of the interrogation region resulting from non-linear motion of the transducer. As a result, the area represented by each pixel or datum of the extracted data may be compressed or expanded as compared to other data of the extracted data.

The relative distances between pixel pairs is determined and accounted for in the transformation. The processing system 802 determines the distance between pixels in a frame of data or the extracted data as a function of beamformation, scan conversion processing and/or estimated local or global motion. The extracted data is warped or transformed as a function of various differences in distance represented by the data. For example, see U.S. Pat. No. 5,910,114, assigned to the assignee of the present invention, the disclosure of which is incorporated herein by reference.

The compounded image 910 is generated from the transformed extracted data. Since the compounded data represents scans of the same area from more than one direction, speckle and shadows or artifacts are reduced.

If the compounded image 910 or an associated extended field of view image is undesirable, such as blurred or smeared, the image may be regenerated. For example, an extended field of view image is generated in real-time as a patient is scanned. If the extended field of view image becomes undesirable, the user reverses the movement of the transducer. The processing system 802 removes the effects of frames of data associated with positions scanned a second time during the reversed motion. In response to the reversed estimated motion, the processing system 802 recombines frames of data without frames of data associated with positions being removed. Additional frames of data are added to the extended field of view data once the transducer motion is reversed back to the original scan direction. As a result, the extended field of view data for the most recently scanned regions is reacquired. In other embodiments, the user resets one or more parameters of the scan or compounding as part of the reversal of transducer motion. In yet other embodiments, the extended field of view or compounded image 910 is regenerated in response to user input other than transducer movement, such as moving a track-ball or mouse or depressing a button.

Additional processing may be performed to any of the compounded sub-set of data, the extended field of view data or frames of data absent compounding for the extended field of view. In one embodiment, the extracted compounded data, frames of data before compounding or the extended field of view data is passed through a two-dimensional high-pass filter. The filter is designed to make image details and edges sharper. The two-dimensional sharpening filter may have the following structure:

$$\text{SHARP} = \begin{bmatrix} -0.33 & -0.33 & -0.33 \\ -0.33 & 3.67 & -0.33 \\ -0.33 & -0.33 & -0.33 \end{bmatrix} + (0.33s)$$

where the parameter, s, ranges from 0 to 1 and may be a function of the frame number, n. The filter characteristics are normalized so that the sum of all the coefficients equals one. Other coefficients may be used. The smaller the parameter s, the sharper the output image. For filtering the extended field of view data in real time, the first frames of data correspond to a small frame number n, so the extended field of view data has more noise. Accordingly, the parameter s is large to prevent over sharpening. Alternatively, the parameter s is derived from a consideration of various factors, including transducer frequency and scan depth. Higher probe frequency and larger scanning depth make the speckle size smaller (i.e., less pixels per resolution cell). In other words, the filter is adaptive to the change of relative resolution.

Other additional processing includes spatial or temporal filtering of the frames of data before compounding with other frames of data associated with a different transducer position. The frames of data may be processed differently for data to be used for estimating motion and data used for compounding. Areas associated with scanned features, such as shadowed regions or tissue features, may be identified and emphasized for estimating motion.

Any of the various motion estimate, compounding, filtering or other processes discussed above may be changed by the user. The compounded image is regenerated in response to the changed parameters. The extended field of view image or other images may also be regenerated.

While the invention has been described above by reference to various embodiments, it will be understood that many changes and modifications can be made without departing from the scope of the invention. For example, the compounded data may comprise Doppler velocity, energy, variance and/or B-mode intensity data. As yet another example, triggering of acquisition of frames of data may be provided as a function of the breathing or heart cycle. For heart cycle triggering, the heart cycle is determined as a function of a signal from an EKG device or as a function of variance in acquired data.

It is therefore intended that the foregoing detailed description be understood as an illustration of the presently preferred embodiments of the invention, and not as a definition of the invention. It is only the following claims, including all equivalents, that are intended to define the scope of this invention.

What is claimed is:

1. A method for displaying a plurality of images of an extended field of view associated with azimuthal transducer movement, the method comprising:
   (a) compounding a first frame of data with a second frame of data in an overlapping region where the first and second frames are associated with first and second different transducer positions, respectively;
   (b) displaying an extended field of view image responsive to (a); and
   (c) displaying a compounded image comprising a sub-set of data corresponding to the extended field of view image, the compounded image adjacent to the extended field of view image.

2. The method of claim 1 further comprising:
   (d) displaying a first image responsive to the first frame of data absent the compounding of (a) adjacent to the compounded image.

3. The method of claim 1 further comprising:
   (e) extracting data for the compounded image associated with a section of the extended field of view image corresponding to the first transducer position.

4. The method of claim 3 further comprising:
   (e) transforming the extracted data.

5. The method of claim 1 wherein (a) comprises compounding the first and second frames of data where the first frame of data comprises sector formatted data.

6. The method of claim 1 wherein (a) comprises compounding first and second frames of data where the first frame of data comprises a sub-set of a scanned frame of data.

7. The method of claim 6 wherein the sub-set of the scanned frame of data comprises data associated with an azimuthally centered section of the scanned frame of data.

8. The method of claim 6 further comprising:
   (d) controlling an amount of data within the sub-set of the scanned frame of data in response to user input.

9. A method for displaying a plurality of images of an extended field of view associated with azimuthal transducer movement, the method comprising:
   (a) compounding a first frame of data with a second frame of data in an overlapping region where the first and second frames are associated with first and second different transducer positions, respectively;
   (b) displaying a compounded image comprising a sub-set of image data responsive to (a); and
   (c) displaying a first image responsive to the first frame of data absent the compounding of (a) adjacent to compounded image.

10. The method of claim 9 further comprising:
    (d) displaying an extended field of view image responsive to (a).

11. The method of claim 10 further comprising:
    (e) extracting data for the compounded image associated with a section of the extended field of view image corresponding to the first transducer position.

12. The method of claim 11 further comprising:
    (f) transforming the extracted data.

13. The method of claim 9 wherein (a) comprises compounding the first and second frames of data where the first frame of data comprises sector formatted data.

14. The method of claim 9 wherein (a) comprises compounding first and second frames of data where the first frame of data comprises a sub-set of a scanned frame of data.

15. The method of claim 14 wherein the sub-set of the scanned frame of data comprises data associated with an azimuthally centered section of the scanned frame of data.

16. The method of claim 14 further comprising:
    (d) controlling an amount of data within the sub-set of the scanned frame of data in response to user input.

17. An apparatus for displaying a plurality of images of an extended field of view associated with azimuthal transducer movement, the apparatus comprising:
    a transducer;
    a processor operable to compound a first frame of data with a second frame of data in an overlapping region where the first and second frames are associated with first and second different transducer positions, respectively;
    a display operable to display a compounded image comprising a sub-set of image data corresponding to the compounded first and second frames of data and to display a first image responsive to the first frame of data absent the compounding of the first and second frames of data, the compounded image adjacent to the first image.

18. The apparatus of claim 17 wherein the display is operable to display an extended field of view image corresponding to the compounded first and second frames of data.

19. An apparatus for displaying a plurality of images of an extended field of view associated with azimuthal transducer movement, the apparatus comprising:
    a transducer;
    a processor operable to compound a first frame of data with a second frame of data in an overlapping region where the first and second frames are associated with first and second different transducer positions, respectively;
    a display operable to display a compounded image comprising a sub-set of image data corresponding to the compounded first and second frames of data and to display a first image responsive to the first frame of data absent the compounding of the first and second frames of data, the compounded image adjacent to the first image.

20. The apparatus of claim 19 wherein the display is operable to display an extended field of view image.

21. A method for displaying an image extracted from extended field of view data associated with azimuthal transducer movement, the method comprising:
    (a) compounding a first frame of data with a second frame of data in an overlapping region where the first and second frames are associated with first and second different transducer positions, respectively; and
    (b) displaying a compounded image comprising a sub-set of data responsive to (a) and corresponding to at least a portion of the overlapping region.

* * * * *